(12) United States Patent
Pham et al.

(10) Patent No.: US 10,368,919 B2
(45) Date of Patent: Aug. 6, 2019

(54) SACRAL-ILIAC STABILIZATION SYSTEM

(75) Inventors: Khiem Pham, Chalfont, PA (US); Mark Salzberger, Sinking Spring, PA (US)

(73) Assignee: GLOBUS MEDICAL, INC., Audubon, PA (US)

(*) Notice: Subject to any disclaimer, the term of this patent is extended or adjusted under 35 U.S.C. 154(b) by 242 days.

(21) Appl. No.: 13/189,084

(22) Filed: Jul. 22, 2011

(65) Prior Publication Data

US 2012/0022595 A1 Jan. 26, 2012

Related U.S. Application Data

(60) Provisional application No. 61/366,815, filed on Jul. 22, 2010.

(51) Int. Cl.
*A61B 17/70* (2006.01)

(52) U.S. Cl.
CPC ...... *A61B 17/7055* (2013.01); *A61B 17/7032* (2013.01)

(58) Field of Classification Search
CPC ............ A61B 17/7055; A61B 17/7044; A61B 17/7049; A61B 17/7032; A61B 17/7059
USPC ........ 606/250–253, 276–278, 286, 329, 271, 606/280, 287, 324, 330
See application file for complete search history.

(56) References Cited

U.S. PATENT DOCUMENTS

| | | | |
|---|---|---|---|
| 4,773,402 A * | 9/1988 | Asher et al. | 606/250 |
| 5,084,049 A | 1/1992 | Asher | |
| 5,127,912 A | 7/1992 | Ray | |
| 5,133,717 A * | 7/1992 | Chopin | 606/301 |
| 5,147,360 A | 9/1992 | Dubousset | |
| 5,300,073 A | 4/1994 | Ray | |
| 5,571,102 A | 11/1996 | Cavagna | |
| 5,622,652 A | 4/1997 | Kucherovsky | |
| 5,993,449 A * | 11/1999 | Schlapfer et al. | 606/60 |
| 6,106,526 A | 8/2000 | Harms | |
| 6,129,730 A * | 10/2000 | Bono et al. | 606/291 |
| 6,132,431 A | 10/2000 | Nilsson | |
| 6,187,005 B1 * | 2/2001 | Brace | A61B 17/7035 606/264 |
| 6,197,028 B1 * | 3/2001 | Ray et al. | 606/301 |
| 6,458,131 B1 * | 10/2002 | Ray | 606/86 A |
| 6,485,491 B1 | 11/2002 | Farris | |
| 6,520,990 B1 | 2/2003 | Ray | |
| 6,648,885 B1 | 11/2003 | Friesem | |
| 6,682,532 B2 * | 1/2004 | Johnson | A61B 17/7007 606/264 |
| 6,755,829 B1 | 6/2004 | Bono | |
| 7,081,117 B2 | 7/2006 | Bono | |
| 7,128,744 B2 * | 10/2006 | Weaver | A61B 17/8057 606/280 |
| 7,232,441 B2 | 6/2007 | Altarac | |
| 7,303,563 B2 | 12/2007 | Poyner | |
| 7,455,684 B2 | 11/2008 | Gradel | |

(Continued)

*Primary Examiner* — Jacquiline T Johanas

(57) ABSTRACT

The present invention provides a sacral-iliac plate having an iliac portion with a first screw hole for receiving a first fastener to secure the iliac portion to the iliac bone. A sacral portion integrated monolithically with the iliac portion is also provided with a second and third screw holes for receiving second and third fasteners to secure the sacral portion to the sacral bone. The sacral portion also includes a tulip for receiving and securing a spinal rod.

12 Claims, 5 Drawing Sheets

(56) References Cited

U.S. PATENT DOCUMENTS

| | | | |
|---|---|---|---|
| 7,575,588 B2 | 8/2009 | Barker | |
| 7,699,872 B2 | 4/2010 | Farris | |
| 7,850,719 B2 * | 12/2010 | Gournay | A61B 17/7037 |
| | | | 606/278 |
| 8,007,499 B2 * | 8/2011 | Piehl | A61B 17/8061 |
| | | | 606/280 |
| 9,585,697 B2 * | 3/2017 | Stachniak | A61B 17/7035 |
| 9,757,154 B2 * | 9/2017 | Donner | A61B 17/1757 |
| 9,872,711 B2 * | 1/2018 | Hynes | A61B 17/7044 |
| 2004/0162558 A1 * | 8/2004 | Hegde et al. | 606/61 |
| 2006/0106382 A1 * | 5/2006 | Gournay | A61B 17/7037 |
| | | | 606/278 |
| 2008/0021454 A1 * | 1/2008 | Chao | A61B 17/7044 |
| | | | 606/250 |
| 2008/0125781 A1 * | 5/2008 | Hoffman | A61B 17/7055 |
| | | | 606/331 |
| 2009/0125067 A1 * | 5/2009 | Mazzuca | A61B 17/7055 |
| | | | 606/280 |
| 2010/0082067 A1 * | 4/2010 | Kondrashov | 606/264 |
| 2010/0114177 A1 * | 5/2010 | Piehl | A61B 17/7055 |
| | | | 606/286 |
| 2012/0022595 A1 * | 1/2012 | Pham | A61B 17/7032 |
| | | | 606/278 |
| 2014/0249581 A1 * | 9/2014 | Stachniak | A61B 17/7035 |
| | | | 606/264 |

* cited by examiner

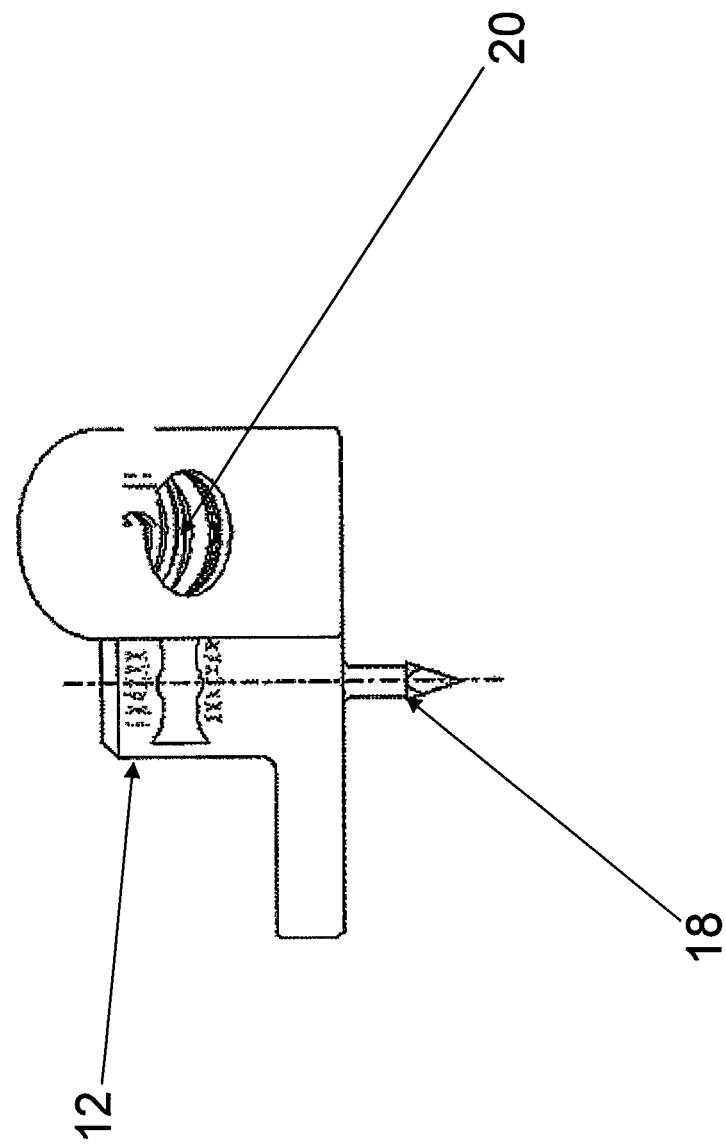

SACRAL-ILIAC STABILIZATION SYSTEM

CROSS REFERENCE TO RELATED APPLICATIONS

This application claims priority to Provisional Application Ser. No. 61/366,815 filed on Jul. 22, 2010, incorporated herein in its entirety.

FIELD OF THE INVENTION

The present disclosure generally relates to a fixation device for positioning a plate between the sacrum and iliac portion of the human body.

BACKGROUND OF THE INVENTION

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses. Typically, weaknesses in the spine are corrected by using devises that fuse one or more vertebrae together. There is a need stabilizing the iliac portion of the human body to the sacrum portion of the vertebrae to provide additional stability.

SUMMARY OF THE INVENTION

The present invention provides a sacral-iliac plate having an iliac portion with a first screw hole for receiving a first fastener to secure the iliac portion to the iliac bone. A sacral portion integrated monolithically with the iliac portion is also provided with a second and third screw holes for receiving second and third fasteners to secure the sacral portion to the sacral bone. The sacral portion also includes a tulip for receiving and securing a spinal rod.

BRIEF DESCRIPTION OF THE DRAWINGS

FIG. 3 is back view of the sacral-iliac plate illustrated in FIG. 1-3;

DETAILED DESCRIPTION OF THE ILLUSTRATED EMBODIMENTS

While it is apparent that the invention disclosed herein is well calculated to fulfill the objects stated above, it will be appreciated that numerous modifications and embodiments may be devised by those skilled in the art.

Figure 1:
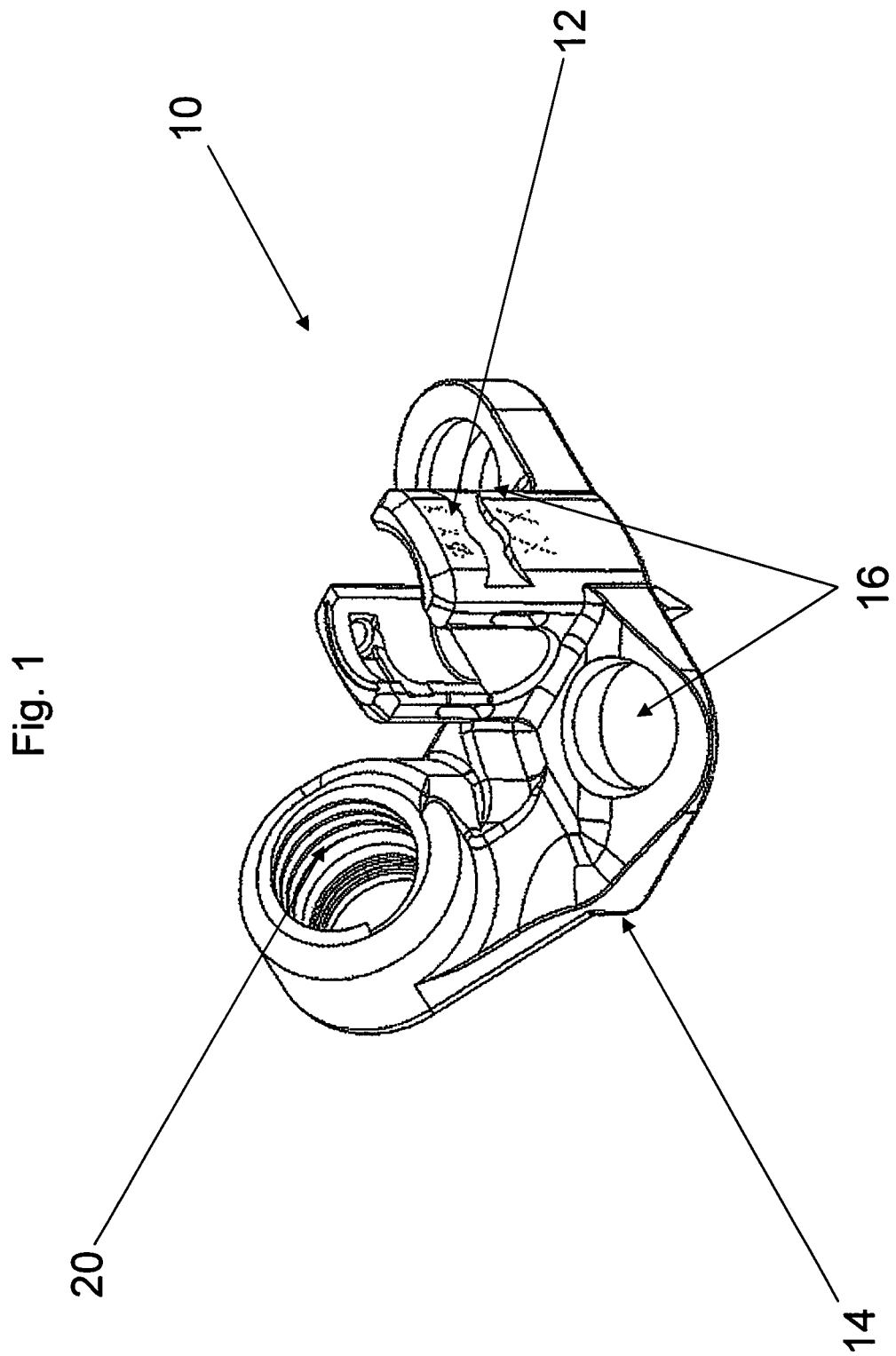
FIG. 1 is a perspective view of a sacral-iliac plate according to one embodiment of the present invention.

FIGS. 1-3 illustrate the sacral-iliac plate according to one embodiment of the present invention. Specifically, the sacral-iliac plate of the present invention enables surgeons the ability to use the plate for various medical conditions such as spondylolisthesis, neuromuscular scoliosis, degenerative lumbosacral joint, and pelvic obliquity.

Turning now to FIG. 1, a sacral-iliac plate 10 is shown. The plate 10 is a unitary plate with an integrated tulip 12 that provides support and stability across the sacral iliac joint configured to receive a spinal rod within the tulip 12. The plate 10 is further configured with an integrated tulip feature which allows the spinal rod to be top loaded.

Figure 2B:
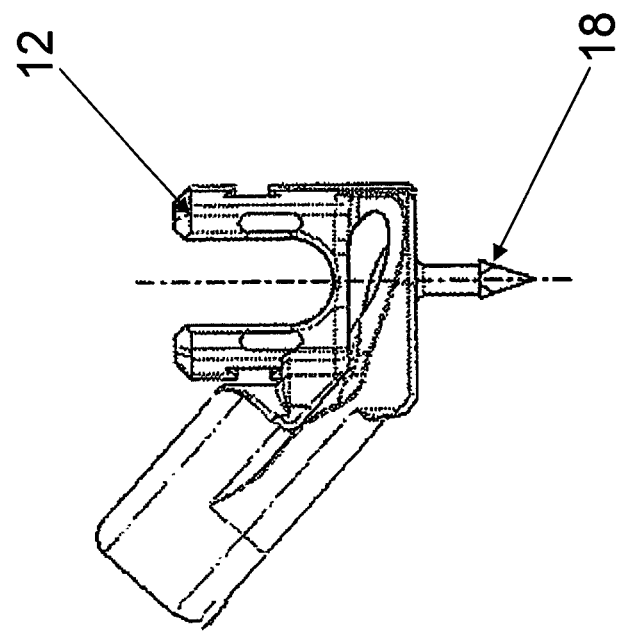
FIGS. 2A and 2B are side views of the sacral-iliac plate of the present invention.
Figure 2A:
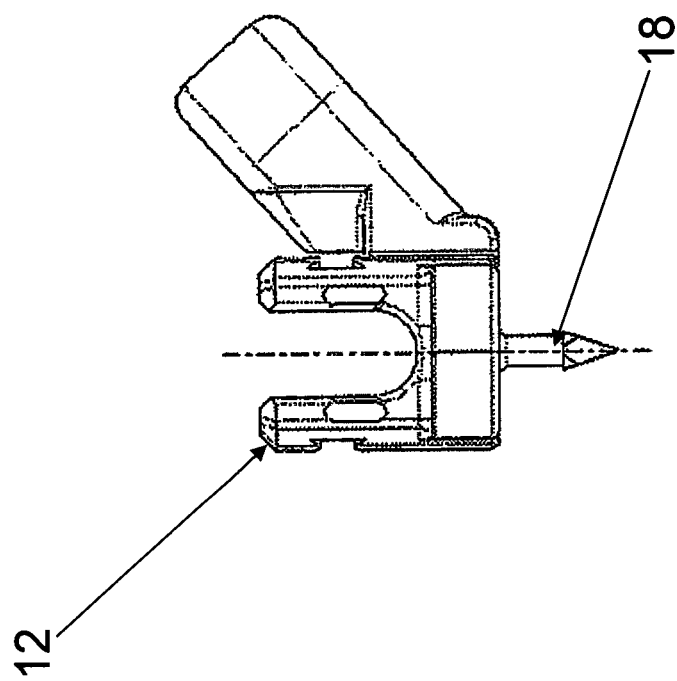

As best seen in the FIGS. 2A and 2B, the sacral iliac plate 12 includes a generally L-shaped body 14 with the integrated tulip head 12 interposed between and generally in line with two sacral holes 16. A sharp prong 18 or barb extends downward from the undersurface to facilitate temporary fixation during installation. The sacral holes 16 are non-threaded holes and are configured to receive screws there through to attach the sacral iliac plate to a sacrum bone of a patient. The tulip head 12 extends upward from the superior surface of the plate body 14 and forms a channel in the direction of the sacral holes 16 for receiving a spinal rod and a cap (not shown) may be used to secure the rod therein. In the embodiment illustrated, the sacral holes 16 are configured to be in-line with the tulip, however, the sacral holes 16 may be offset to accommodate the anatomy of the sacral bone. An iliac portion of the L-shaped body 14 extends laterally outward and angled upwards from a lower portion of the sacral iliac plate 12. The angulation of iliac portion of the plate 12 with respect to the lower portion is generally between 35° to 50° and preferably 40°.

The iliac portion has a threaded hole 20 that is configured to receive a screw therein to fix the iliac portion of the sacral iliac plate to the iliac bone of a patient. The iliac screw head has corresponding threads to mate with the threaded portion of the iliac screw hole 20. It should be noted that although in the present embodiment, the iliac portion of the plate 12 is provided with a threaded hole 20, a non-threaded hole may be utilized.

Figure 4:
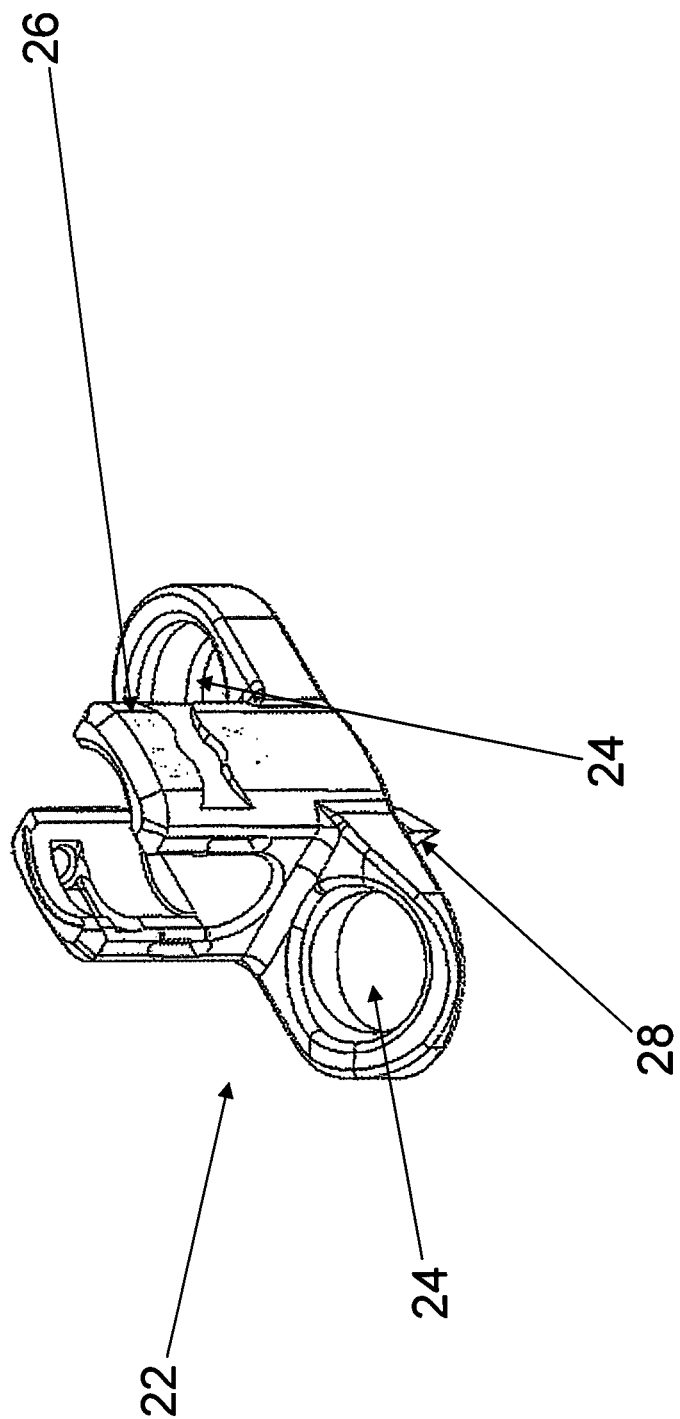
FIG. 4 is a perspective view of another embodiment of a sacral-iliac plate according to the present invention.
Figure 5B:
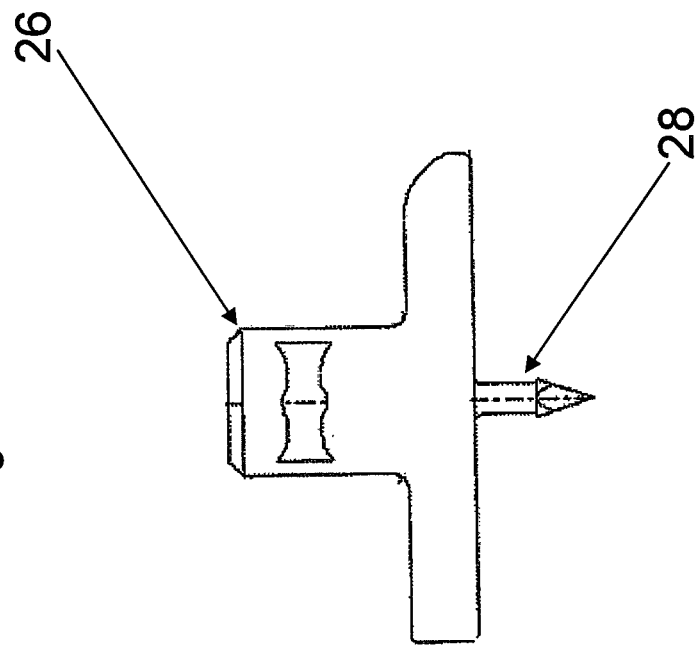
FIG. 5B is a side view of the sacral-iliac plate shown in FIG. 4.
Figure 5A:
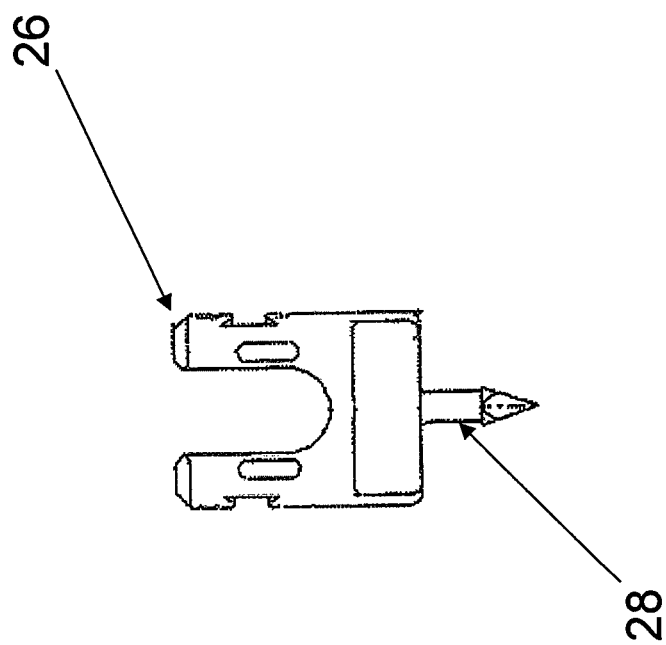
FIG. 5A is a front view of the sacral-iliac place shown in FIG. 4.

FIGS. 4, 5A and 5B illustrate another embodiment of the present invention. In this embodiment, the sacrum plate 22 is provided with two screw holes 24 having a tulip 26 configured between the two screw holes 24. The tulip 26 is designed and configured to receive a spinal rod and a locking cap. The plate is also provided with a sharp prong or barb 28 which extends downward from the undersurface to facilitate temporary fixation during installation. It should be noted that although a single prong is illustrated, multiple prongs may be used to more securely fixate the plate to the sacrum.

The various features and embodiments of the invention described herein may be used interchangeably with other feature and embodiments. Finally, while it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments which come within the spirit and scope of the present invention.

The invention claimed is:

1. A sacral-iliac plate comprising:
   an iliac portion having a first screw hole for receiving a first fastener to secure the iliac portion to the iliac bone;
   a sacral portion integrated monolithically with the iliac portion having a second and third screw holes for receiving a second and third fasteners to secure the sacral portion to the sacral bone, wherein the first screw hole differs from the second and third screw holes, wherein the first screw hole is threaded and the second and third screw holes are non-threaded,
wherein the sacral portion comprises a tulip for receiving and securing a spinal rod,
wherein the tulip is integrated with the sacral portion,
wherein the tulip extends upward from a superior surface of the sacral-iliac plate and forms a channel for receiving the spinal rod in a top-loading manner, the channel configured to extend at least partially along a length of the spinal rod towards the second and third sacral screw holes,
wherein the first and second screw holes are in line along a first axis,
wherein the second and third screw holes are in line with the tulip along a second axis,
wherein the first axis and the second axis are generally perpendicular,
wherein the tulip is positioned in between the second and third screw holes, and the channel of the tulip is positioned in line with the second and third screw holes, and
wherein the iliac portion is angled between 35° to 50° with respect to the sacral portion,
wherein the sacral portion extends from a first end to a second end, wherein the sacral portion includes a first portion extending from the first end to a base of the tulip and a second portion extending from the second end to the base of the tulip, the first portion includes the second screw hole and the second portion includes the third screw hole,
wherein the first portion has a first thickness that is less than a second thickness of the second portion, wherein the second thickness of the second portion is measured from an inferior surface of the sacral-iliac plate to the superior surface of the sacral-iliac plate adjacent the tulip,
wherein a prong is disposed directly underneath the tulip and configured to facilitate temporary fixation during installation of the plate.

2. The sacral-iliac plate according to claim 1, wherein the spinal rod is configured to be secured within the tulip with a locking cap.

3. The sacral-iliac plate according to claim 1, further comprising the first fastener, wherein the first fastener is configured with a threaded head to engage with the threaded first screw hole.

4. The sacral-iliac plate according to claim 1, wherein the iliac portion is angled at 40° with respect to the sacral portion.

5. A sacral-iliac plate comprising:
an iliac portion having a first screw hole for receiving a first fastener to secure the iliac portion to the iliac bone; and
a sacral portion integrated monolithically with the iliac portion having a second and third screw holes for receiving a second and third fasteners to secure the sacral portion to the sacral bone, wherein the first screw hole differs from the second and third screw holes, wherein the first screw hole is threaded and the second and third screw holes are non-threaded,
wherein the sacral portion comprises a tulip for receiving and securing a spinal rod,
wherein the tulip is integrated with the sacral portion,
wherein the tulip extends upward from a superior surface of the sacral-iliac plate and forms a channel for receiving the spinal rod in a top-loading manner, the channel configured to extend at least partially along a length of the spinal rod towards the second and third sacral screw holes,
wherein the tulip is positioned in between the second and third screw holes, and the channel of the tulip is positioned in line with the second and third screw holes, and
wherein the iliac portion and the sacral portion form a generally L-shape,
wherein the sacral portion extends from a first end to a second end, wherein the sacral portion includes a first portion extending from the first end to a base of the tulip and a second portion extending from the second end to the base tulip, the first portion includes the second screw hole and the second portion includes the third screw hole,
wherein the first portion has a first thickness that is less than a second thickness of the second portion, wherein the second thickness of the second portion is measured from an inferior surface of the sacral-iliac plate to the superior surface of the sacral-iliac plate adjacent the tulip,
wherein a prong is disposed directly underneath the tulip and configured to facilitate temporary fixation during installation of the plate.

6. The sacral-iliac plate according to claim 5, wherein the second and third screw holes are in line with the tulip along a second axis.

7. The sacral-iliac plate according to claim 5, wherein the spinal rod is configured to be secured within the tulip with a locking cap.

8. The sacral-iliac plate according to claim 5, further comprising the first fastener, wherein the first fastener is configured with a threaded head to engage with the threaded first screw hole.

9. The sacral-iliac plate according to claim 5, wherein the iliac portion is angled between 35° to 50° with respect to the sacral portion.

10. The sacral-iliac plate according to claim 5, wherein the iliac portion is angled at 40° with respect to the sacral portion.

11. A method of stabilizing a spine comprising:
accessing the sacrum and iliac portions of the spine;
positioning a sacral-iliac plate on a portion of the sacrum and a portion of the iliac bone; and
securing the sacral iliac plate to the portion of the sacrum and the iliac bone;
wherein the sacral-iliac plate comprises:
an iliac portion having a first screw hole for receiving a first fastener to secure the iliac portion to the iliac bone; and
a sacral portion integrated monolithically with the iliac portion having a second and third screw holes for receiving a second and third fasteners to secure the sacral portion to the sacral bone, wherein the first screw hole differs from the second and third screw holes, wherein the first screw hole is threaded and the second and third screw holes are non-threaded,
wherein the sacral portion comprises a tulip for receiving and securing a spinal rod,
wherein the iliac portion and the sacral portion form a generally L-shape,
wherein the tulip is positioned in between the second and third screw holes, and
wherein the tulip extends upward from a superior surface of the sacral-iliac plate and forms a channel for receiving the spinal rod in a top-loading manner, the channel configured to extend at least partially along a length of the spinal rod towards the second and third sacral screw holes, and the channel of the tulip is positioned in line with the second and third screw holes wherein the sacral portion extends from a first end to a second end, wherein the sacral portion includes a first portion extending from the first end to tulip and a second portion extending from the second end to the tulip, the first portion includes the second screw hole and the second portion includes the third screw hole, wherein the first portion has a thickness that is less than a second thickness of the second portion, wherein the second thickness of the second portion is measured from an inferior surface of the sacral-iliac plate to the superior surface of the sacral-iliac plate adjacent the tulip, wherein a prong is disposed directly underneath the tulip and configured to facilitate temporary fixation during installation of the plate.

12. The method according to claim 11, wherein the iliac portion is angled 40° with respect to the sacral portion.

* * * * *